United States Patent [19]
Kim et al.

[11] Patent Number: 6,001,986
[45] Date of Patent: Dec. 14, 1999

[54] **ANTIVIRAL PROTEINS, AMARANDIN 1 AND 2, FROM *AMARANTHUS VIRIDIS*, DNAS ENCODING THEREFROM**

[75] Inventors: Yong Sig Kim; Sun Chung Park; Soo Kyung Oh, all of Kwangju; Hosull Lee, Taejeon; Jeong Woo Cho; Chang H. Chung, both of Kwangju, all of Rep. of Korea

[73] Assignee: Korea Kumbo Petrochemical Co., Ltd., Seoul, Rep. of Korea

[21] Appl. No.: 08/916,443

[22] Filed: Aug. 22, 1997

[51] Int. Cl.$^6$ ..................................................... C12N 15/29
[52] U.S. Cl. ..................... 536/23.6; 435/320.1; 435/471; 435/252.3
[58] Field of Search ........................... 536/23.6; 800/205, 800/DIG. 9; 435/320.1, 471, 252.3

[56] References Cited

U.S. PATENT DOCUMENTS 5,501,970 3/1996 Legname et al. .
5,529,932 6/1996 Lorenzetti et al. .

OTHER PUBLICATIONS

Napoli et al. The Plant Cell. 1989. vol. 2: 278–289.
Linthorst et al. The Plant Cell. 1989. Voll. 1(3): 285–291.
Carvalho et al. The EMBO. Journal. 1992. vol. 11: 5995–5602.
Sudan. GeneBank Accession Number: X54873, NCBI. 1991.
Arcaina et al. GeneBank Accesion Number: L79873. Jul. 1996.
Hudson, J.B., *Antiviral Compounds from Plants,* 1990, CRC Press, Inc., pp. 167–177.
Habuka, N., et al., *J. Biol. Chem.,* 265:19, p. 10988–10992, Jul. 5, 1990.
Stirpe, F., *Bio/Technology,* 10:405–412. Apr. 1992.
Prestle, J., et al., *Nucl. Acids Res.,* 20:12, pp. 3179–3182, 1992.

*Primary Examiner*—Elizabeth F. McElwain
*Assistant Examiner*—Ousama Zaghmout
*Attorney, Agent, or Firm*—Kenyon & Kenyon

[57] ABSTRACT

DNA sequences encoding antiviral proteins, amarandin 1 and 2 from *Amaranthus viridis* is disclosed. Expression vectors encoding amarandin 1 or 2 and transformed host cells are also disclosed.

14 Claims, 8 Drawing Sheets

AMARANDIN 1

| Enzyme | Positions | Enzyme | Positions | Enzyme | Positions |
|---|---|---|---|---|---|
| AflII | 646 | AluI | 43, 64, 35, 402, 476, 796, 828 | AseI | 424 |
| Asp718I | 31 | AsuI | 646 | BanI | 31 |
| BsmAI | 272 | BstXI | 590 | CfoI | 284, 481, 514 |
| ClaI | 335 | DdeI | 23, 155, 830 | DpnI | 85, 220, 370, 379 |
| EarI | 274 | EcoRI | 636 | Fnu4HI | 136, 202, 511, 819 |
| HinPII | 284, 481, 514 | HinfI | 257, 569, 735 | HphI | 18, 535 |
| KpnI | 31 | Ksp632I | 274 | MaeI | 478, 650 |
| MaeII | 270, 296, 912 | MfeI | 606 | MseI | 80, 413, 425, 667, 740, 749, 882 |
| NlaIII | 729, 771 | NlaIV | 31 | PleI | 257 |
| RsaI | 32, 268 | Sau3AI | 85, 220, 370, 379 | SstIII | 270, 296, 912 |
| TaqI | 69, 336, 346, 381 | TspEI | 121, 452, 551, 607, 637, 654, 665, 716 | | |

FIG. 2A

AMARANDIN 2

| Enzyme | Positions | Enzyme | Positions | Enzyme | Positions |
|---|---|---|---|---|---|
| AflI | 805 | AluI | 49, 202, 223, 294, 530, 561, 635, 735, 955, 987 | AseI | 583 |
| AsuI | 805 | BclI | 353 | BsmAI | 431 |
| BstXI | 749 | CfoI | 443, 640, 673 | ClaI | 494 |
| DdeI | 314, 989, 1000 | DpnI | 135, 354, 379, 538, 628 | DraI | 679 |
| EarI | 433 | Fnu4HI | 295, 361, 670 | HinPII | 443, 640, 673 |
| HinfI | 728, 894 | HphI | 694 | Ksp632I | 433 |
| MaeI | 637, 809 | MaeII | 429, 455, 476, 1071 | MfeI | 765 |
| MseI | 253, 368, 572, 584, 680, 826, 899, 908, 1041 | NlaIII | 75, 351, 888, 93, 0 | NlaIV | 415 |
| RsaI | 105, 427 | Sau3AI | 135, 354, 379, 538, 628 | SstIII | 429, 455, 476, 1071 |
| TaqI | 228, 495, 540 | TspEI | 97, 237, 251, 611, 710, 766, 813, 824, 875, 1011 | | |

FIG.2B

```
AMARANDIN 1
LOCUS       AF000937    946 bp           mRNA         PLN    31-DEC-1997
DEFINITION  Amaranthus viridis AMARANDIN1(ARP1) mRNA, partial cds.
ACCESSION   AF000937
KEYWORDS    .
SOURCE      Amaranthus viridis.
  ORGANISM  Amaranthus viridis
            Eukaryotee; mitochondrial eukaryotes; Viridiplantee;
            Charophyta/Embryophyta group; Embryophyta; vascular
            plants; seed plants; Magnoliophyta; Magnoliopsida;
            Caryophyllales; Amaranthaceae; Amaranthus.
REFERENCE   1 (bases 1 to 946)
  AUTHORS   Kim,Y., Park,S., Oh,S., Chung,C. and Cho,J.
  TITLE     Direct Submission
  JOURNAL   Submitted (22-APR-1997) Kumho Life 6 Environmental Science
            Laboratory, 572 Sangamdong Kwangsanku, Kwangju 506-712,
            Korea
FEATURES             Location/Qualifiers
     source          1..946
                     /organism="Amaranthus viridis"
                     /tissue_type="leaf"
     gene            <1..756
                     /gene="ARP"
     CDS             <1   756
                     /gene="ARP"
                     /note="ribosome inactivating protein; RNA N-
                     glycosidase; antiviral protein"
                     /codon_start=1
                     /product="AMARANDIN1"
```

/translation="ADLTFTVTKSGTSQSYSTLLNSFRDKVKDPKLTGTYGFQNNLPV

VAAPTTPAKYLYIDIQADNGIITAAFDKNDLYYMGYAHTADGVKKVRLFKGAPTDVKL

IFPDVTNKNNRYYSTITGNYNDLGDRASVGLGAKPLNKFINEEIYTKKKFDITTDKKL

ALMVIQTIAEAARFTYIEGEIVSKFSDNSGFKCNDKAKSLENNWEKTSKTVKNSTGPR

```
IDLELKDENGKVVWKWLQVGELVDVMGILKYLK"
BASE COUNT       362 a     144 c     172 g     268 t
ORIGIN
  1   gcagacctga ctttcacggt gactaagagt ggtaccagcc aaagctactc cacactattg
 61   aatagctttc gagataaagt taagatcca  aaactaacag gaacttatgg atttcaaaac
121   aatttaccag ttgtagctgc acccacaaca cctgctaagt atctttacat tgatattcag
181   gcagatastg gaataatcac tgctgcattt gataaaaacg atctctatta tatgggttat
241   gctcacactg cagatggagt caagaaggta cgtctcttca aaggcgctcc aactgacgta
301   aagttgattt ttcccgatgt tacaaataaa aacaatcgat attattcgac cattactgga
361   aactataatg atcttggaga tcgagcctct gtagggttgg gagctaaacc acttaataag
421   tttattaatg aagaaatcta tacaaaaaag aaatttgaca ttacaacaga taaaaagcta
481   gcgcttatgg tcatccaaac tattgcagaa gcagcgcgat ttacatatat tgaaggtgaa
541   atcgtgagta aattcagtga taatagtgga ttcaaatgta atgataaagc caagtcactg
601   gagaacaatt gggaaaaaac cagtaaaact gtcaagaatt ctactggtcc tagaattgat
661   ttggaattaa aagatgaaaa tggtaaagta gtctggaaat ggttacaagt cggagaatta
721   gttgatgtca tggggattct taaatatctt aagtageatg gaaatgtctt catgtcatat
781   aagtatctgt ttagtagctg ataatgaata atgaaaatgc agcaataagc taagatatta
841   catattgttg taagttcaaa gttgtaacga cttttgttt  tttaatactt ctatccccta
901   aaaatatttt cacgtaaaaa aaaaaaaaaa aaaaaaaaaa aaaaa
```

FIG.3A

AMARANDIN 2

```
LOCUS       AF004389      1116 bp    mRNA            PLN      31-DEC-1997
>DEFINITION Amaranthus viridis ribosome inactivating protein
            AMARANDIN2(ARP2) mRNA, complete cds.
>ACCESSION  AF004389
>KEYWORDS   .
>SOURCE     Amaranthus viridis.
> ORGANISM  Amaranthus viridis
>           Eukaryotae; mitochondrial eukaryotes; Viridiplantee;
>           Charophyta/Embryophyta group; Embryophyta; vascular
            plants; seed plants; Magnoliophyta; Magnoliopsida;
            Caryophyllales; Amaranthaceae; Amaranthus.
>REFERENCE  1 (bases 1 to 1116)
> AUTHORS   Kim,Y.S., Park,S.C., Oh,S.K., Cho,J.W. and Chung,C.H.
> TITLE     Direct Submission
> JOURNAL   Submitted (16-MAY-1997) Kumho Life & Environmental
            Science Laboratory, 572 SangamHong Kwangsanku, Kwangju
            506-712, Korea
>FEATURES            Location/Qualifiers
>     source         1..1116
>                    /organism="Amaranthus viridis"
>                    /tissue_type="leaf"
>     gene           <1..>909
>                    /gene="ARP2"
>     CDS            <1..>909
>                    /gene="ARP2"
                     /function="RNA N-glycosidase; antiviral"
                     /note="ribosome inactivating protein"
                     /codon_start=1
                     /product="AMARANDIN2"
                     /translation="IPSLYFLHCF LIPSCESLSI ILFINMKMKK
ITNLVYILVA ITTSVIFQWT CNAVNPTFVVTMSATNKSYS TLLSSFRDEI QDKKLKGTYG
FQNDLPVVAA PTKPAKYLYI DIQADKGMITAAFNKNDLYY MGYAHTADGA KKVRLFKGAP
TDVRLIFPDV TNINNRYYST ITGNYNELGDRASVGLGAKP LNKFINEEIY TKKKFDIQTD
QKLALMVIQT IAEAARFKYI EGEIVAKFSDNSGFKANPKA KSLENNWDKT SETVKASTGP
RIDLELTYGN GNVVWKWFQV GELVDVMGIL"
BASE COUNT       181 a    103 c    92 g    167 t
ORIGIN
    1 ATCCCATCAT TATATTTCCT CCATTGTTTT CTTATCCCAT CCTGTGAAAG CTTGAGCATT
   61 ATATTGTTCA TCAACATGAA GATGAAAAAG ATAACAAATT TGGTGTACAT TTTGGTAGCC
  121 ATTACAACAA GTGTGATCTT TCAATGGACT TGCAATGCAG TAAATCCAAC ATTCGTTGTG
  181 ACAATGAGTG CTACCAATAA AAGCTACTCC ACTCTATTGA GTAGCTTTCG AGATGAAATT
  241 CAAGATAAAA AATTAAAAGG AACTTATGGA TTTCAAAACG ATTTACCAGT TGTAGCTGCA
  301 CCAACAAAAC CTGCTAAGTA TCTTTACATT GATATTCAGG CAGATAAGGG CATGATCACT
  361 GCTGCGTTTA ATAAAAACGA TCTCTATTAT ATGGGTTATG CTCACACTGC TGATGGAGCC
  421 AAGAAAGTAC GTCTCTTCAA AGGCGCTCCA ACTGACGTAA GGTTGATTTT TCCCGACGTT
  481 ACAAATATAA ACAATCGATA TTATTCTACC ATTACTGGAA ACTATAATGA GCTTGGAGAT
  541 CGAGCCTCTG TAGGGTTGGG AGCTAAACCA CTTAATAAGT TTATTAATGA AGAAATCTAT
  601 ACAAAAAAGA AATTTGACAT ACAAACAGAT CAAAAGCTAG CGCTTATGGT CATCCAAACT
  661 ATTGCAGAAG CAGCGCGATT TAAATATATT GAGGGTGAAA TCGTGGCTAA ATTTAGTGAT
  721 AATAGTGGAT TCAAAGCTAA TCCTAAAGCC AAATCACTGG AGAACAATTG GGATAAAACC
  781 AGTGAGACTG TCAAGGCATC TACTGGTCCT AGAATTGATT TGGAATTAAC ATATGGAAAT
  841 GGTAATGTAG TATGGAAATG GTTTCAAGTC GGAGAATTAG TTGATGTCAT GGGGATTCTT
  901 AAATATCTTA AGTAGAATGG AAATGTCTTC ATGTCATATA AGTATCTGTT TAGTAGCTGA
  961 TAATGAATAA TGAAAATGCA ACAATAAGCT AAGATATTAC TTAGGGTTGT AATTTCAAAG
 1021 TTGTAACGAC TTTTGTATGT TTAATACTTC TATCCCCTAA AAAATATTGC ACGTTTCCAA
 1081 AAAAAAAAAA AAAAAAAAAA AAAAAAAAAA AAAAAA
```

ANTIVIRAL PROTEINS, AMARANDIN 1 AND 2, FROM *AMARANTHUS VIRIDIS*, DNAS ENCODING THEREFROM

BACKGROUND OF THE INVENTION

The present invention relates to the entire nucleotide sequences of cDNAs that are encoding amarandin 1 and 2, ribosome-inactivating proteins having antiviral activity, of *Amaranthus viridis*.

According to ANTIVIRAL COMPOUNDS FROM PLANTS, 1st ed., CRC Press, Inc., (1990) and Bio/Technology (1992) 10:405–412, the ribosome-inactivating proteins (RIPs), classified as type 1 and 2, have antiviral and abortifacient activities with N-glycosidase activity which cleave the N-glycosidic bond of adenine in a specific ribosomal RNA sequence. Interest in ribosome-inactivating proteins stems from their potential utilization in agriculture and medicine, due to their antiviral activity and antifungal activity. Ribosome-inactivating proteins can be utilized either for the production of the multiple virus-resistant crops or for the inhibition of virus replication comprising virus-induced human diseases, like HIV-1 replication, selectively in cell cultures. Moreover, one can custom design extremely specific and very effective small peptide conferring an antiviral activity, from the basis of RIP structure, to interfere with the penetration stage of certain myxoviruses.

During our screening studies searching for new RIP we found that *Amaranthus viridis* crude extracts displayed both translational inhibitory and antiviral activities against plant viruses.

SUMMARY OF THE INVENTION

It is therefore, an object of the present invention to provide a method for isolating and purifying antiviral proteins, amarandin 1 and 2, of *Amaranthus viridis*.

It is another object of the present invention to isolate the DNAs that encode amarandin 1 and 2 of *Amaranthus viridis*.

It is still another object of the present invention to provide a hybrid vector containing said DNAs.

It is as yet another object of the present invention to provide a transformed host that contains said DNAs or hybrid vector that is capable of expressing said DNAs.

In accomplishing these and other objects and advantages, there has been provided DNAs that comprise DNA sequences that encode amarandin 1 and 2 or fragments thereof.

In accordance with another aspect of the present invention, there has been provided DNAs as above, the fragments further comprising DNA sequence that is capable of influencing the expression of DNA sequences.

In accordance with yet another object of the present invention, there has been provided DNAs as above, the DNA sequences of which are capable of encoding N-terminal amino acid sequences of amarandin 1 and 2, respectively, $^1$Ala-Asp-Leu-Thr-Phe-Thr-Val-Thr-Lys-Asp-Gly$^{11}$- (amarandin 1) (SEQ ID NO:1), and $^1$Val-Asn-Pro-Thr-Phe-Val-Val-Thr-Met-Ser$^{10}$- (amarandin 2) (SEQ ID NO:2).

which are identified as ribosome-inactivating protein having antiviral activity.

In accordance with a further object of the present invention, there has been provided hybrid vectors comprising DNAs as above, said vectors being capable of being transferred to and replicating in a host.

In accordance with yet a further object of the present invention, there has been provided hybrid vectors as above, said vectors being plasmid pRSET.

In accordance with another object of the present invention, there has been provided transformed hosts comprising the hybrid vectors as above, said host being capable of expressing the DNAs.

In accordance with still another object of the present invention, there has been provided transformed hosts comprising the DNAs as above, said hosts being capable of expressing the DNAs.

Further advantages, objects and features of the present invention will become apparent from the following detailed description. It should be understood, however, that the detailed description, while indicating preferred embodiments of the invention, is giving by way of illustration only, since various changes and modifications within the spirit and scope of the invention will become apparent to those skilled in the art from this detailed description.

BRIEF DESCRIPTION OF THE DRAWING

The file of this patent contains at least one drawing executed in color. Copies of this patent with the color drawing will be provided by the Patent and Trademark Office upon request and payment of the necessary fee.

FIG. 2A shows a diagram of the restriction map of amarandin 1 nucleotide sequence of *Amaranthus viridis*, approximately 753 base pairs of maximum open reading frame in length;

FIG. 2B shows a diagram of the restriction map of amarandin 2 nucleotide sequence of *Amaranthus viridis*, approximately 825 base pairs of maximum open reading frame in length.

FIG. 3A shows a diagram of the entire nucleotide sequence of cDNAs and their deducted amino acid sequences of amarandin 1, antiviral protein of *Amaranthus viridis*;

FIG. 3A shows a diagram of the entire nucleotide sequence of cDNAs and their deducted amino acid sequences of amarandin 2, antiviral protein of *Amaranthus viridis*.

DETAILED DESCRIPTION OF THE PREFERRED EMBODIMENTS

Figure 1A:
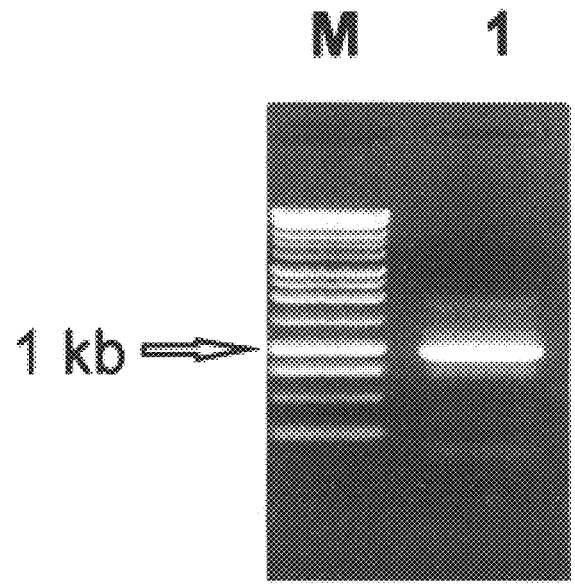
FIG. 1A shows amplification products from total cDNA library with vector primer, T7, with degenerate primer ADL and VNP based on peptide sequences of amarandin 1, where the PCR products were analyzed on 1% agarose gel electrophoresis M, DNA molecular weight markets 1, T7 and ADL PCR products.
Figure 1B:
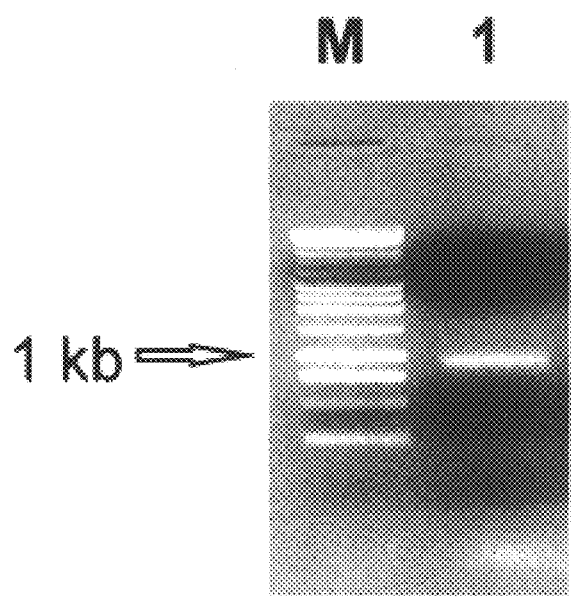
FIG. 1B shows amplification products from total cDNA library with vector primer, T7, with degenerate primer ADL and VNP based on peptide sequences of amarandin 2, where the PCR products were analyzed on 1% agarose gel electrophoresis M, DNA molecular weight markets 1, T7 and VNP PCR products.
Figure 4A:
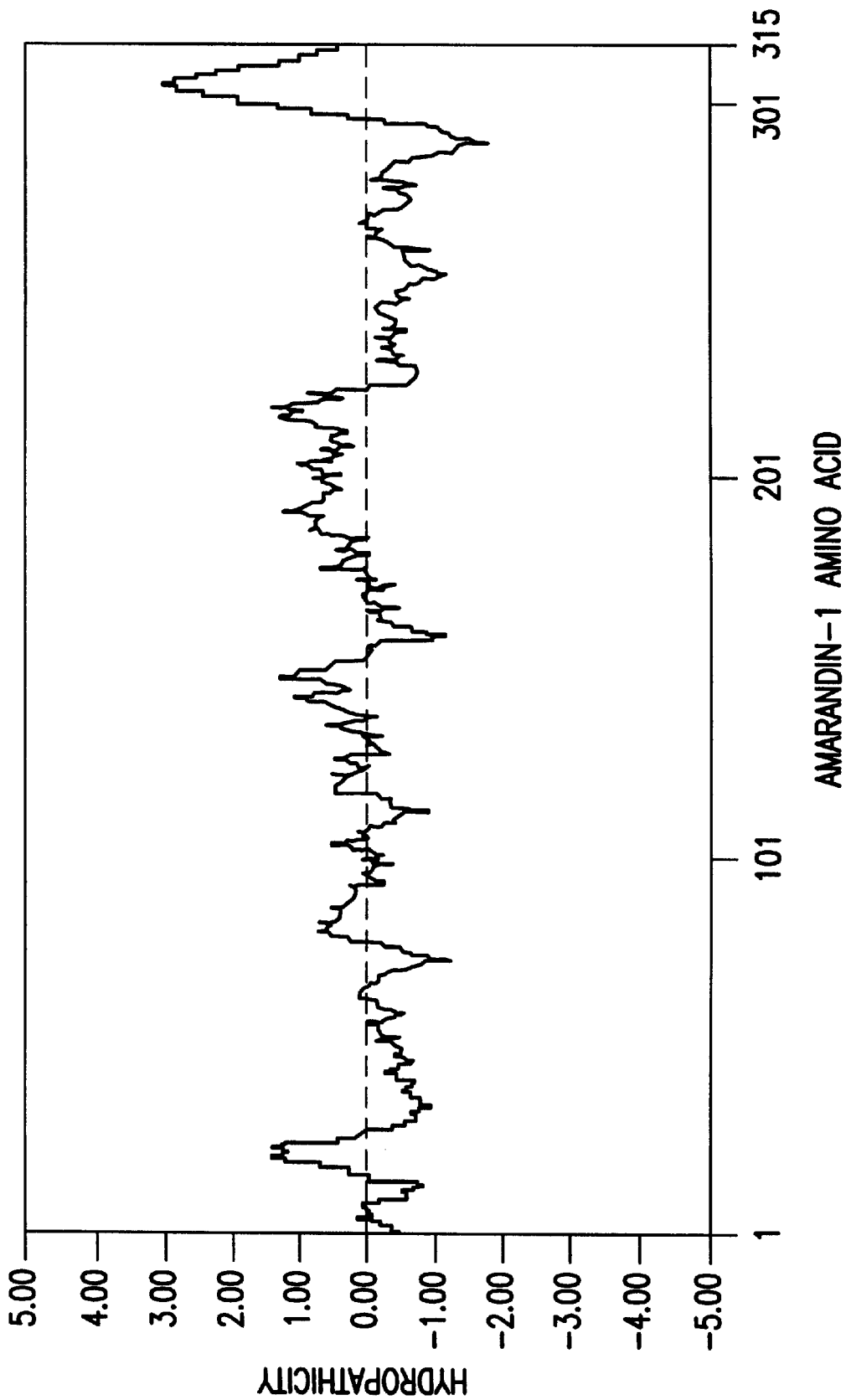
FIG. 4A is a diagram of the hydropathicity of the amino acid sequences of amarandin 1.
Figure 4B:
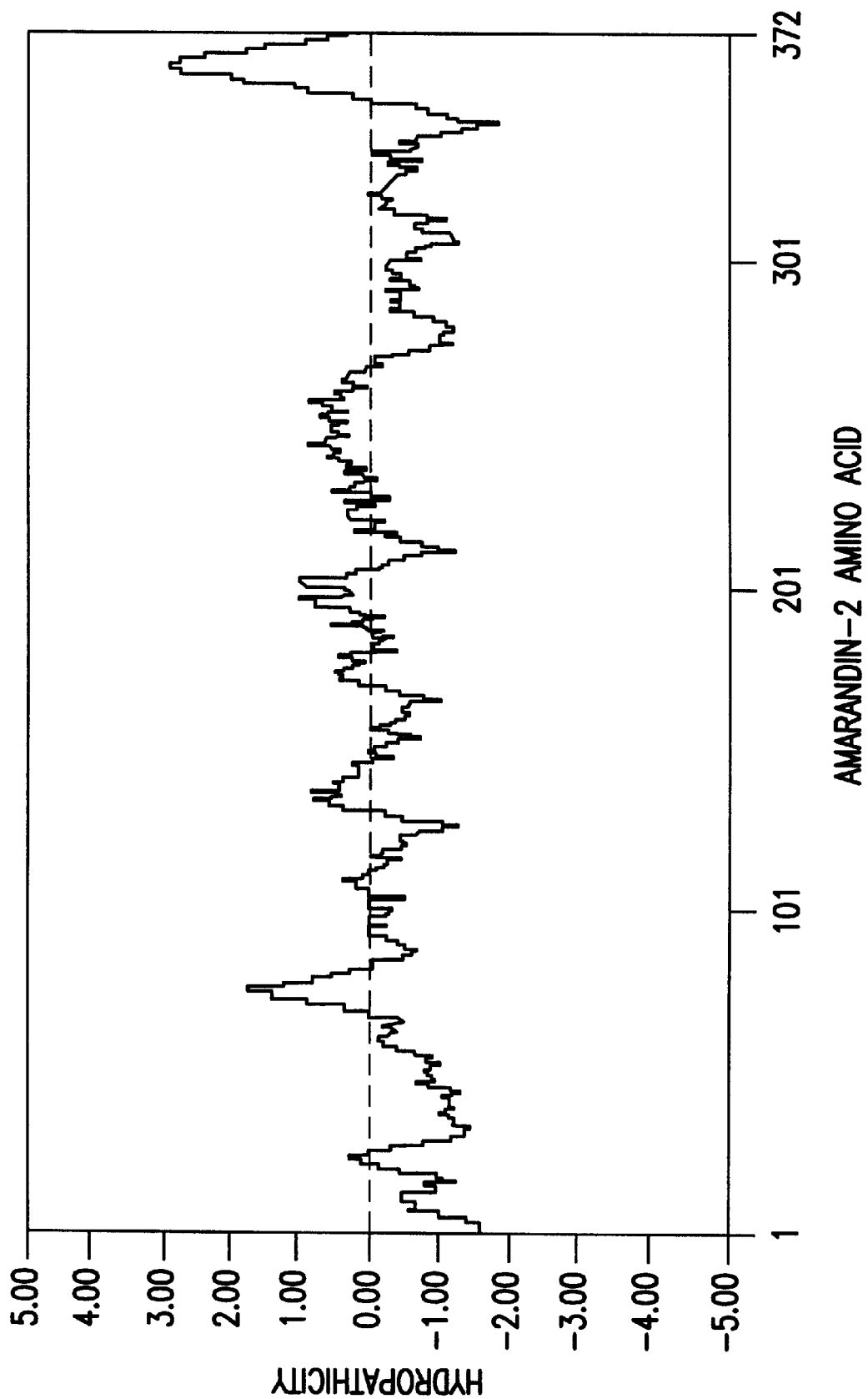
FIG. 4B is a diagram of the hydropathicity of the amino acid sequences of amarandin 2.
Figure 5A:
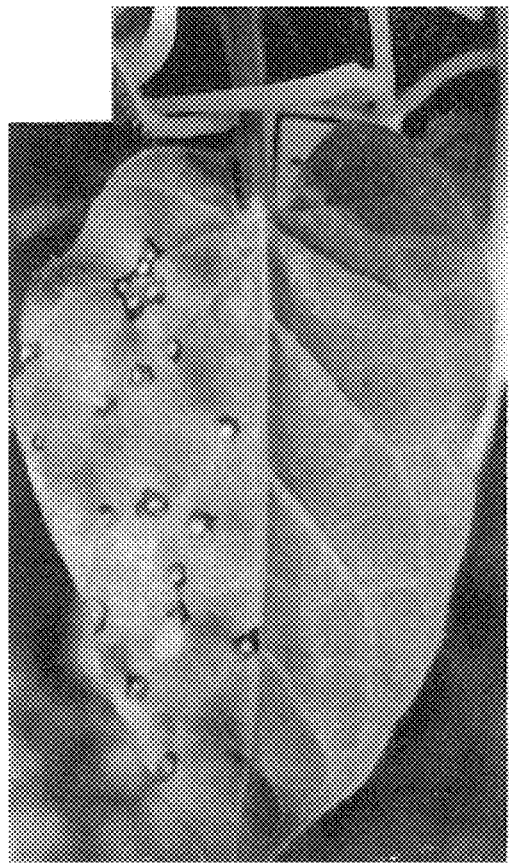
FIG. 5A shows antiviral activity of amarandin 2 against tobacco mosaic virus where the right side of the leaf is treated with 0.3 µg/ml Amarandin 2 and the left side of the leaf is treated with buffer as control, and the local lesions were counted at 1 week postinoculation.
Figure 5B:
FIG. 5B shows antiviral activity of amarandin 1 against tobacco mosaic virus where the right side of the leaf is treated with 0.3 µg/ml Amarandin 1 and the left side of the leaf is treated with buffer as control, and the local lesions were counted at 2 weeks postinoculation.

The present invention relates to the entire nucleotide sequences of cDNAs that are encoding amarandin 1 and 2, ribosome-inactivating proteins having antiviral activity, of *Amaranthus viridis*.

A number of phylogentically diverse plants has been reported to contain proteins which acts as powerful inhibitors of eukaryotic ribosomes. Ribosome-inactivating proteins (RIPs) are classified as type 1 and 2. Type 1 RIP has a unique enzymic polypeptide chain with N-glycosidase activity on the ribosomal RNA that irreversibly impair protein synthesis by enzymatically modifying the EF-2-dependent GTPase activity of the subunit. Type 2 RIP is consisting in two polypeptide chains linked by a disulfide bonding, A-chain being the enzymic chain able to attack the 60S ribosomal subunit and B-chain being a lectin able to recognize membrane sugars, mostly galactose residues. Type 1 RIPs are relatively abundant and to date nearly 30 have been isolated, the best known of which are saporin and pokeweed antiviral protein. The pokeweed antiviral protein, the first of the non-toxic proteins to be purified, was shown to inhibit protein synthesis in the host cells. Subsequently it was found that both the toxins and the 'A-chain-like' proteins, like pokeweed antiviral protein (PAP), the wheat-germ inhibitor, the *Momordica charantia* inhibitor and gelonin, strongly inhibit an eukaryotic ribosome. An extract from *Bryonia dioica* (bryony) seeds, which inhibits protein synthesis, also had antiviral activity, and an extract from *Dianthus caryophyllus* leaves, whose antiviral activity was known, had a strong inhibitory effect on protein synthesis. Type 2 RIPs, which can enter cells through the interaction of their lectin moiety with the cell membrane, are among the most potent natural toxins because of their capacity to bind most intact cells, the best known of which is ricin.

Although RIPs have similar physicochemical properties and seem to have identical effects on protein synthesis, ribosomes from various plants, protozoa and prokaryotes have different sensitivity patterns to RIP. For this reason, RIP could be useful tools to study functional and structural properties of ribosomes as well as its implication for the therapeutic agent. Also, interest in RIP stems from their potential utilization in agriculture, due to their antiviral activity and antifungal activity.

Inventors have isolated and purified amarandin 1 and 2 ribosome-inactivating proteins having antiviral activity from *Amaranthus viridis* leaves, an edible crop in Korea. The first 10 amino-terminal amino acid sequences of amarandin 1 and 2 are determined as, $^1$Ala-Asp-Leu-Thr-Phe-Thr-Val-Thr-Lys-Asp-Gly$^{11}$- (amarandin 1) (SEQ ID NO:1), and $^1$Val-Asn-Pro-Thr-Phe-Val-Val-Thr-Met-Ser$^{10}$- (amarandin 2) (SEQ ID NO:2).

cDNA nucleotide sequences of amarandin 1 and 2 in full length, which are capable of encoding the full length amino acid sequences of amarandin 1 and 2 (hereafter "amarandin 1 and 2 DNA sequences"), accessing antiviral activity, have been determined and deposited at the GenBank (National Center for Biotechnology Information, National Library of Medicine, National Institute of Health, 9600 Rockville Pike, Bethesda, Md. 20892, U.S.A.) with the accession No. AF000937 and AF004389, respectively. Inventors also have identified the restriction enzyme sites in amarandin 1 and 2 DNA sequences and have provided a hybrid vector and a transformed host, respectively, that contain the amarandin 1 and 2 DNA sequences. They have 33% amino acid sequence homology with the other RIPs. There is 89% amino acid sequence identity between amarandin 1 and 2, and they are immunologically cross-reactive each other. Also, there are regions of potential glycosylation site in amarandins, -N-X-T/D: one at the 213th position from N-terminus in amarandin 1, and one at the 31st and 231th positions from N-terminus in amarandin 2. In amarandin 2, there is a signal peptide sequence of 28 amino acid residues at the N-terminus of the polypeptide chain and it is characterized by the presence of hydrophobic amino acids helping the translocation of the protein. Preferably signal peptide sequence in amarandin 2 is:

MKMKKITNLVYILVAITTSVIFQWTCNA (SEQ ID NO:4).

Amarandin 1 and 2 can be extracted from leaf tissue of the plant *Amaranthus viridis* wherein they are present in two forms having different molecular weight, respectively 28,000 and 30,000; said molecules seem to be two different proteins although no definitive conclusion has been drawn. The biochemical characteristics of these two proteins are similar: alkaline isoelectric point is remarkably basic for both (pI~9.5); Their action are enzymatic, as the IC$_{50}$ (50% inhibitory concentration) value calculated on rabbit reticulocyte lysate are identically of the order of 10$^{-11}$ M. As little as 0.3 ng/ml of amarandin 1 and 2 is inhibitory, amarandin 1 and 2 are very effective inhibitory of ribosome function in vitro, apparently by interfering with EF-2 (elongation factor 2) mediated translocation of the nascent peptide chain along the ribosome.

Also, amarandin 1 and 2 of *Amaranthus viridis* were shown to reduce the infectivity of tobacco mosaic virus (TMV) and other plant viruses, although interestingly the antiviral property was not demonstrable in the host plant itself. The antiviral spectrum of amarandins may include TMV, watermelon mosaic virus, zucchini mosaic virus, cauliflower mosaic virus, potato virus X and Y, potato leafroll virus, odontoglossum ringspot virus, and cucumber mosaic viruses etc., all of which are readily quantitated by mixing with the above proteins and rubbing onto susceptible leaves. There was actually a 95% decrease in the production of extracellular infectious virus, suggesting that a late stage of the virus replication cycle was inhibited.

Within the context of the present invention, amarandin proteins refer to the enzymes that mediate either the cleavage of N-glycosidic bond of a specific position in plant viral RNA, resulting in the inhibition of plant viral infection. A hybrid vector as used herein refers to a vector formed by ligation of DNA from a plasmid, Agrobacterium or other vectors with DNA or cDNA from Amaranthus or other organisms that are capable of producing amarandin 1 and 2, such plants or other organisms being collectively referred to herein as plant materials.

In one embodiment of the present invention, plant material, e.g., *Amaranthus viridis*, is used to produce cDNA library. cDNA library is constructed that is based upon mRNA sequences isolated from total RNA from *Amaranthus viridis*. A first strand cDNA can be synthesized enzymatically using the isolated mRNA as a template, an oligo dT sequence as a primer and a reverse transcriptase as the enzyme. After construction of the first strand cDNA, a second strand cDNA can be synthesized enzymatically using the first strand cDNA as a template and a DNA polymerase as the enzyme. The resulting double-stranded cDNA molecules are inserted into a suitable vector, to produce a cDNA library.

The resulting cDNA library may be capable of expressing amarandin 1 and 2 DNA sequences in suitable host, e.g. *E. coli*. Microbes containing amarandin DNA sequences can be identified using antibodies to amarandin 1 and 2 or alternatively, using a nucleic acid probe specific for the amarandin 1 and 2 DNA sequences. The amarandin 1 and 2 DNA sequences containing cells can then be propagated, and large amounts of DNA sequence encoding amarandin 1 and 2 can be extracted.

In a preferred embodiment of the present invention, nucleic acid probes for the identification of amarandin 1 and 2 DNA sequences are produced in the following manner: amarandin proteins are purified by conventional laboratory techniques, e.g., as according to the column chromatography. The amino acid sequence of at least a portion of the purified amarandin proteins can be determined and, based upon an identified amino acid sequence, a corresponding nucleotide sequence that is capable of encoding the amino acid sequence can be predicted and nucleic acid probes can be constructed synthetically based upon the predicted sequence. Because of the degeneracy of the genetic code, however, prediction of the nucleotide sequence on the basis of the amino acid sequence may lead to several possible nucleotide sequences. A collection of different nucleic acid sequences that comprise the various possible nucleotide sequences can be constructed, labeled, and used to screen a DNA library containing the amarandin 1 and 2 DNA sequences.

Plant DNA or DNA from other organisms that hybridizes with a labeled nucleic acid probe specific for the amarandin 1 and 2 DNA sequences can be identified and isolated. The isolated DNA can be ligated to a vector DNA to produce a hybrid vector. The hybrid vector can be used to transform a competent host and to induce the production of amarandin 1 and 2 in the host. One such plasmid, pRSET, constructed from *Amaranthus viridis* cDNA and the vector pRSET and inserted into bacteria has been deposited according to the Budapest Treaty at the KCTC under accession KCTC0344BP and KCTC0345BP with the Korea Research Institute of Bioscience and Biotechnology, Korean Collection for Type Cultures, located at #52, Oun-dong, Yusong-ku, Taejón 305–333, Republic of Korea on Jun. 20, 1997. The microorganism *E. coli BL*21 (DE3)pLES 97011 is assigned Accession No. KCTC 0344BP. The microorganism *E. coli* XL1-Blue pLES 97020 is assigned Accession No. KCTC 0345BP.

A vector that is suitable for use in the context of the present invention can be a plasmid or a virus that is capable of being transferred into a host cell or of infecting a host cell and of replicating in a host cell. In a preferred embodiment, a suitable vector is one that is capable of carrying as an insert of an entire amarandin 1 and 2 DNA sequences in a non-essential region of the vector DNA.

A suitable transformed host is one that is capable of expressing the amarandin 1 and 2 DNA sequences. In a preferred embodiment, a suitable transformed host is capable of producing 28,000–30,000 Da of amarandin 1 and 2 in a significant amount before transformation and becomes capable of producing amarandin 1 and 2 in a significant amount after transformation. Such a host may be a plant, a bacterium or a fungus. The plant host may be an annual plant such as tobacco species, a grass species or a perennial plant species. The bacterium can be any bacterium, e.g., *E. coli*, a Bacillus species or an Agrobacterium species. The fungus is selected from the group consisting of Aspergillus species.

In another embodiment of the present invention, the DNA fragment that contains the amarandin 1 and 2 DNA sequences can be ligated to a suitable promoter so as to place the gene under the control of the promoter. A suitable promoter is one that is capable of functioning in a transformed host. For example, if the host to be transformed is a plant, the amarandin 1 and 2 DNA sequences can be ligated to a plant promoter such as Pnos, the promoter for the nopaline synthetase; if the host to be transformed is a bacterium, the amarandin 1 and 2 DNA sequences can be ligated to a bacterium promoter such as trp or tac promoter of *E. coli*. In the alternative, the amarandin 1 and 2 DNA sequences can be ligated to a virus promoter such as the 35S promoter of cauliflower mosaic virus or to a tap1 wound-inducible promoter.

In a preferred embodiment of the present invention, a cDNA library, instead of a genomic DNA library, is constructed using mRNA isolated from total RNA. Total RNA is obtained from plant materials by conventional laboratory techniques.

The isolation of mRNA herein capitalizes on the presence of a poly A tail at the 3' end of the mRNA. The 3' tail is utilized to separate mRNA from the other RNA species. Separation is achieved by chromatography on an Oligotex column by binding of the poly A tail of mRNA with the T residues on the column. The unbound RNA can be washed free of the column and the mRNA can be eluted by buffers that destabilize the A-T duplex. The RNA concentration is then determined spectrophotometrically.

The integrity of the mRNA preparation, i.e., whether it is full length or simply a small fragment with a 3' poly A tail, is determined by in vitro translation of the mRNA. A full-length mRNA can be selected and used to construct a cDNA library. The amarandin 1 and 2 DNA sequences in this library can be detected utilizing either nucleic acid probes or antibodies if the cDNA library expresses the cDNA.

The plant materials that are used for the isolation of mRNA can be from any plants or organisms that are capable of synthesizing amarandin 1 and 2. For example, since Amaranthus seedlings produce amarandin 1 and 2 from the very earliest stages of growth, mRNA capable of encoding amarandin 1 and 2 can be obtained from Amaranthus seedlings. The isolated mRNA is then used as a template for synthesis of first strand cDNA molecules. The first-strand cDNA is, in turn, used as a template in a second-strand DNA synthesis utilizing, e.g., DNA polymerase I. In this manner, cDNA library can be generated.

To find the nucleotide sequence in the cDNA library that is capable of encoding amarandin 1 and 2, a complementary nucleic acid probe can be used that contains a predicted nucleotide sequence based upon a known amino acid sequence of the amarandin proteins. In the alternative, polyclonal or monoclonal antibodies to amarandins can be produced in experimental animals or in hybridomas, respectively, and used to identify those transformed host cells that produce amarandin 1 and 2.

In a preferred embodiment of the present invention, at least a portion of the amino acid sequence of the purified amarandin proteins is determined by sequencing. Nucleic acid probes based upon the predicted nucleotide sequences can be constructed in accordance with conventional laboratory techniques. In formulating the sequences to be constructed, different strategies can be adopted.

DNA from the clone that carries amarandin 1 and 2 DNA sequences and that reacts positively with the amarandin 1 and 2 DNA sequences specific probe can be isolated and ligated to another vector after removing the amarandin 1 and 2 DNA sequences. Removal of the amarandin 1 an 2 DNA sequences is accomplished by digesting the DNA from the original positive clone with an enzyme, e.g., EcoRI, that frees the Amaranthus cDNA from the vector DNA. This method of gene removal is feasible because when the Amaranthus cDNA library is constructed, the cDNA is inserted into the proper vector at an EcoRI restriction site. Digestion of the vector that contains cDNA insert with EcoRI, therefore, frees the insert from the viral vector sequences.

The amarandin 1 and 2 DNA sequences isolated in the above described manner can be subcloned into another plasmid for the production of large quantities of these genes. In one embodiment of the present invention, the gene can be subcloned in plasmid pRSET and maintained in *E. coli*. The cells containing the pRSET plasmid with the amarandin 1 an 2 DNA sequences are propagated to produce large quantities of the amarandin 1 an 2 DNA sequences. These DNAs can be extracted from the transformed hosts in accordance with conventional laboratory techniques.

Restriction map of the amarandin 1 and 2 DNA sequences can be constructed by treating the DNA sequence with restriction enzymes, e.g., amarandin 1-AflI, AluI, AseI, Asp718I, AsuI, BanI, BsmAI, BstXI, CfoI, ClaI, DdeI, DpnI, EarI, EcoRI, Fnu4HI, HinPlI, HinfI, HphI, KpnI, Ksp632I, MaeI, MaeII, MfeI, MseI, NlaIII, NlaIV, PleI, RsaI, Sau3AI, SstIII, TaqI, TspEI, and KLESIN2—AflI, AluI, AseI, AsuI, BclI, BsmAI, BstXI, CfoI, ClaI, DdeI, DpnI, DraI, EarI, Fnu4HI, HinPlI, HinfI, HphI, Ksp632I, MaeI, MaeII, MfeI, MseI, NlaIII, NlaIV, RsaI, Sau3AI, SstIII, TaqI, TspEI, and determining the size of the DNA fragments generated therefrom. Based upon the identity of the restriction enzymes that are capable of digesting the amarandin 1 and 2 DNA sequences and the size of the DNA fragments each of these enzymes generates, a restriction map of the amarandin 1 and 2 DNA sequences can be generated.

As described in the present invention, cDNA cloning for antiviral proteins, amarandin 1 and 2, and their deduced amino acid sequences will provide the valuable information on the further detailed structure-function relationship as well as understanding on the molecular action mechanism of RIPs against the viral infections. Therefore, the present invention is very important to inhibit virus replication comprising virus-induced human diseases, like HIV-1 replication, selectively in cell cultures, as well as to develop the broad spectrum of virus-resistance to the economically valuable crops, or to custom design extremely specific and very effective small peptide conferring an antiviral activity to interfere with the penetration stage of certain myxoviruses.

The following example is given by way of illustration to facilitate a better understanding of the present invention and are not intended to limit the scope thereof.

EXAMPLE 1
Purification and Characterization of Amarandin 1 and 2 of *Amaranthus viridis*

Amarandin 1 and 2 were isolated from leaves of *Amaranthus viridis* by CM-Sepharose column chromatography followed by Mono-S on FPLC at 4° C. as follows: 1 kg of leaves were cut into small pieces and then ground in a mortar and pestle and extracted with 1 L of 10 mM sodium phosphate (pH 6.8), 0.1 mM 2-mercaptoethanol. The extract was filtered through a cheesecloth, and the fluid was then centrifuged at 10,000×g for 20 min at 4° C. The supernatant was fractionated with ammonium sulfate precipitation at 0–30%, 30–80% and 80–100%. The precipitates obtained were redissolved in 10 mM sodium phosphate buffer (pH 6.8) and dialyzed overnight against the same buffer. The dialyzed solution was then applied to CM-Sepharose column chromatography (30×2.5 cm) equilibrated with the extraction buffer. The column was washed with the same buffer until absorbance reached the base line. The bound protein was linear-gradiently eluted with the same buffer containing 250 mM NaCl. The peak containing the protein was concentrated with an Amicon YM 10 membrane and applied to Mono-S fitted with a FPLC apparatus and equilibrated and eluted with 10 mM sodium phosphate (pH 7.0) containing 250 mM NaCl. This chromatographic step resolved two main protein bands of amarandin. The fraction containing the protein peak was pooled, dialyzed against Milli-Q purified water, and finally stored at −70° C. until it will be used.

Analyses of proteins by SDS-PAGE were carried out as described by Laemmli using 12% polyacrylamide gels. The isloelectric point of amarandin was measured by native isoeletric focusing on a 5% polyacrylamide gel containing 2% carrier Ampholyte from pH 3 to 10. Protein bands were detected by staining with 0.1% Coomassie blue dye.

The ability of amarandin 1 and 2 to inhibit protein synthesis in a cell-free system was estimated by using rabbit reticulocyte lysate system kit (Boehringer Mannhein, Germany) with L-[$^{35}$S] methionine according to the manufacturer's manual. After the translation reaction was completed, 2 μl from the reaction mixture were further incubated with 98 μl of 1 M NaOH and 2% $H_2O_2$ at 37° C. for 10 min. After 10 min incubation, 0.9 ml of ice-cold 25% (w/v) trichloroacetic acid was added, and the precipitates were collected by filtration on glass filters (Whatmann GF/C). Radioactivity on the filter was measured by scintillation counting.

Also, antiviral activities of amarandins were determined by applying TMV on the surface of tobacco leaves. TMV was mixed with the amarandins to be tested or with an equal volume of water as a control. Inoculum, containing 600 grit carborundum as an abrasive, was rubbed on to leaves of the local lesion host *Nicotiana glutonosia* in a greenhouse at 25° C. Each treatment was replicated 5 times and randomized on whole leaves of the test plants. Lesions were counted after 14 days of infection.

EXAMPLE 2
Amino Acid Sequencing Analysis of Amarandin 1 and 2

Amarandins were subjected to SDS-PAGE in the presence of 2-mercaptoethanol. Protein electroblotted onto PVDF membranes were detected by staining with 0.2% Coomassie Blue R-250 (w/v) in methanol:water:acetic acid (50:40:10) for 3 min. The membrane was washed in methanol:water:acetic acid (48:47:5), and the protein band was cut out of the PVDF and applied to Beckman 890C amino acid Sequencer equipped with a Sequemat P-6 auto-converter. An Altex 345C HPLC and a Hewlett-Packard 3390A integrator were used to analyze the products, according to the methods of Tarr.

EXAMPLE 3
Isolation of Total RNA from *Amaranthus viridis*

Ten grams of leaves from three month old *Amaranthus viridis* were frozen in liquid nitrogen and ground in mortar and pestle to a fine powder. The grounded material was transferred to a chilled Corex tube to which was added 10 ml of ice cold extraction buffer containing 200 mM Tris at pH 7.0, 5 mM EDTA, 0.1 mM LiCl and 1% SDS followed by heating at 65° C. for 10 min. The suspension was centrifuged at 20° C. for 20 min at 15,000 rpm. The supernatant fraction was collected. Total RNA was precipitated by the addition of 0.5 volume of phenol and chloroform followed by 2 M LiCl treatment. After dissolved with water, total RNA was precipitated with the addition of two volume of ethanol at −20° C. followed by centrifugation at 12,000 rpm, 4° C., for 10 min. All glasswares and solutions were previously treated with 0.1% diethylpyrocarbonate and sterilized.

EXAMPLE 4
Isolation of mRNA from *Amaranthus viridis*

Poly-A$^+$ RNA was isolated and purified with Oligotex™ mRNA Midi kit (QIAGEN, Germany), according to the manufacturer's directions. Total RNA was loaded to the Oligotex™ column equilibrated with 2×binding buffer after total RNA was heated at 65° C. for 5 minutes. The Oligotex™ column was twice washed with 0.5 ml of the washing buffer followed by 20 μl of the elution buffer. Poly-A$^+$ RNA obtained was precipitated with 2.5 volume of absolute ethanol at −20° C. and centrifuged at 12,000 rpm, 4° C. for 10 min. Poly-A$^+$ RNA precipitated was dissolved with 20 μl of TE buffer containing 10 mM Tris-Cl, pH 8.0, and 1 mM EDTA after washing with 70% ethanol. Poly-A$^+$ RNA concentration was determined spectrometrically at 260 nm. All procedures were performed with the operator wearing surgical rubber gloves to minimize nuclease contamination of the mRNA preparation.

EXAMPLE 5
Synthesis and Cloning of cDNA from *Amaranthus viridis* cDNA library from *Amaranthus viridis* was constructed with Uni-ZAP™ cDNA library kit (Stratagene, U.S.A.), according to the manufacturer's manual. The first-strand cDNA was synthesized from the reaction mixtures of 5 μg of poly-A$^+$ RNA, oligo (dT)$_{12-18}$, murine reverse transcriptase, dNTP, BSA, and DTT. In order to synthesize double-stranded cDNA, the first-strand cDNA synthesized was blunted at cDNA termini with the addition of *E. coli* RNase H, *E. coli* DNA polymerase I, and dNTP at 16° C. for 3 h followed by treating the dNTP mixture with Pfu DNA polymerase at 65° C. for 10 min.

EXAMPLE 6
Ligation of cDNA into Uni-ZAP™ ZAP Vector

The termini of cDNA synthesized were ligated to the EcoRI adapter for the insertion of cDNA to the vector. cDNA synthesized was reacted with the addition of EcoRI adapter, ATP, T4 DNA ligase at 12° C. overnight followed by further reaction with the addition of T4 DNA kinase and ATP at 37° C. for 30 min for the ligation of the EcoRI adapter. cDNA was purified with Sephacryl S-500 spin column, and its signal was confirmed on 1.0% agarose gel electrophoresis. Above 1 kb of cDNA fractions was used for further experiments. The insertion of cDNA was resulted from the reaction of the mixtures containing 200 ng of cDNA, 1 μg of vector DNA (Stratagene) and T4 DNA ligase at 4° C. for 48 h.

EXAMPLE 7
Construction and the Amplification of cDNA Library

The Uni-ZAP™ vector DNA was packaged by using Gigapack II packaging extract containing phage ghost (Stratagene). The packaging extract was reacted by the addition of recombinant vector at 22° C. for 2 h. The reaction solution was adjusted up to 500 μl of final volume with SM buffer supplemented with 10 μl of chloroform, and was immediately used or stored at 4° C. until it will be used. Total plaque-forming unit (pfu) of recombinant cDNA library was obtained from $10^{-2}$–$10^{-6}$ fold diluted solution. 200 μl of *E. coli* strain XL1-Blue MRF' were incubated with cDNA library at 37° C. for 15 min, and plated to reach $10^6$ pfu on plate of 150 mm in diameter. The plate supplemented with 5 ml of SM buffer was incubated at 4° C. overnight after reacted the plate at 37° C. for 12 h. The supernatants was obtained from the reacted SM buffer by centrifuging at 12,000 rpm for 10 min, and stored with 100 μl of chloroform at −4° C. The plaque-forming unit was calculated as described in the above.

EXAMPLE 8
Polymerase Chain Reaction for Amarandin Gene Cloning

Two sets of degenerate PCR primers were designed based on the peptide sequence analysis data: ①5'-GCW GAY CTI ACW TTY ACI GT-3' (SEQ ID NO:4) ②5'-GCW GAY CTI ACC TTY ACI GT-3' (SEQ ID NO:5) ③5'-GCC GAY CTI ACW TTY ACI GT-3' (SEQ ID NO:6) ④5'-GCC GAY CTI ACC TTY ACI GT-3' (SEQ ID NO:7) for a peptide ADLT-FTV (SEQ ID NO:8) and ①5'-GTI AAY CCW ACW TTY GTI GT-3' (SEQ ID NO:9) ②5'-GTI AAY CCW ACC TTY GTI GT-3' (SEQ ID NO:10) ③5'-GTI AAY CCG ACW TTY GTI GT-3' (SEQ ID NO:11) ④5'-GTI AAY CCG ACC TTY GTI GT-3' (SEQ ID NO:12) for a peptide VNPTFVV, where I is Inosine (I), R is Adenine (A) or Guanine (G), W is A or Thymine (SEQ ID NO:13) (T), and Y is C or T as the standard nomenclatures. A large scale total phagemid DNA preparation was also made for PCR amplification to isolate partial cDNA piece for further library screening. Phage stock containing total cDNA library was transferred in a form of plasmid from *E. coli* XL1-B MRF' cell into XL1-B SOLR cell via a ExAssist helper. Using this phagemid prep as a template, PCR was performed in 30 cycle of 95° C./30 sec, 50° C./30 sec, 72° C./30 sec with the cocktail mixtures containing 5 μl 10×Taq buffer, 2 μl 25 mM MgCl$_2$, 2 μl 10 pmol each primer, 4 μl 2 mM dNTPs, 0.25 μl cDNA pool, 33.75 μl water by using combinations of vector primers and two degenerate primers.

EXAMPLE 9
Selection of cDNA Library

*E. coli* strain XL1-Blue MRF' as a host cell for phage adhesion was cultured in 50 ml LB medium with 20% maltose, 0.5 ml of 1 M MgSO$_4$ and 50 μg/ml tetracycline. Cell cultures were suspended in 10 mM MgSO$_4$ to make O.D. 0.5 at A$_{600}$. After cultured *E. coli* strain XL1-Blue MRF' with cDNA library at 37° C. for 30 min, the culture mixed with 3 ml of 0.7% LB agar was further incubated on 1.5% LB agar plate at 37° C. for 12 h. 5×$10^4$ cells were used in the first selection, and 1×$10^3$ in second selection. The plates formed phage plaque were stayed at 4° C. for 1 h, and replicated with Hybond-C membrane (Amersham, U.S.A.).

REFERENCES

James B. Hudson, ANTIVIRAL COMPOUNDS from PLANTS, 1990, CRC Press, Inc.
Habuka, N. et al., J. Biol. Chem., 1990, 265:10988–10992.
Stirpe, F. et al., Bio/Technology, 1992, 10:405–412.

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 11 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

Ala Asp Leu Thr Phe Thr Val Thr Lys Asp Gly
             5                   10

(2) INFORMATION FOR SEQ ID NO:2:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

Val Asn Pro Thr Phe Val Val Thr Met Ser
             5                 10

(2) INFORMATION FOR SEQ ID NO:3:

(i) SEQUENCE CHARACTERISTICS:
      (A) LENGTH: 28 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:3:

Met Lys Met Lys Lys Ile Thr Asn Leu Val Tyr Ile Leu Val Ala Ile
                 5                 10              15

Thr Thr Ser Val Ile Phe Gln Trp Thr Cys Asn Ala
            20               25

(2) INFORMATION FOR SEQ ID NO:4:

(i) SEQUENCE CHARACTERISTICS:
      (A) LENGTH: 20 nucleotides
      (B) TYPE: nucleic acid
      (C) STRANDEDNESS: single
      (D) TOPOLOGY: linear (ii) MOLECULE TYPE: genomic DNA (ix) FEATURE:
      (D) OTHER INFORMATION: N is inosine (xi) SEQUENCE DESCRIPTION: SEQ ID NO:4:

GCWGAYCTNA CWTTYACNGT                                           20

(2) INFORMATION FOR SEQ ID NO:5:

(i) SEQUENCE CHARACTERISTICS:

(A) LENGTH: 20 nucleotides
            (B) TYPE: nucleic acid
            (C) STRANDEDNESS: single
            (D) TOPOLOGY: linear (ii) MOLECULE TYPE: genomic DNA (ix) FEATURE:
            (D) OTHER INFORMATION: N is inosine (xi) SEQUENCE DESCRIPTION: SEQ ID NO:5:

GCWGAYCTNA CCTTYACNGT                                                       20

(2) INFORMATION FOR SEQ ID NO:6:

(i) SEQUENCE CHARACTERISTICS:
            (A) LENGTH: 20 nucleotides
            (B) TYPE: nucleic acid
            (C) STRANDEDNESS: single
            (D) TOPOLOGY: linear (ii) MOLECULE TYPE: genomic DNA (ix) FEATURE:
            (D) OTHER INFORMATION: N is inosine (xi) SEQUENCE DESCRIPTION: SEQ ID NO:6:

GCCGAYCTNA CWTTYACNGT                                                       20

(2) INFORMATION FOR SEQ ID NO:7:

(i) SEQUENCE CHARACTERISTICS:
            (A) LENGTH: 20 nucleotides
            (B) TYPE: nucleic acid
            (C) STRANDEDNESS: single
            (D) TOPOLOGY: linear (ii) MOLECULE TYPE: genomic DNA (ix) FEATURE:
            (D) OTHER INFORMATION: N is inosine (xi) SEQUENCE DESCRIPTION: SEQ ID NO:7:

GCCGAYCTNA CCTTYACNGT                                                       20

(2) INFORMATION FOR SEQ ID NO:8:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:8:

Ala Asp Leu Thr Phe Thr Val
              5

(2) INFORMATION FOR SEQ ID NO:9:

(i) SEQUENCE CHARACTERISTICS:
            (A) LENGTH: 20 nucleotides
            (B) TYPE: nucleic acid
            (C) STRANDEDNESS: single
            (D) TOPOLOGY: linear (ii) MOLECULE TYPE: genomic DNA (ix) FEATURE:
            (D) OTHER INFORMATION: N is inosine (xi) SEQUENCE DESCRIPTION: SEQ ID NO:9:

GTNAAYCCWA CWTTYGTNGT                                               20

(2) INFORMATION FOR SEQ ID NO:10:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: genomic DNA (ix) FEATURE:
        (D) OTHER INFORMATION: N is inosine (xi) SEQUENCE DESCRIPTION: SEQ ID NO:10:

GTNAAYCCWA CCTTYGTNGT                                               20

(2) INFORMATION FOR SEQ ID NO:11:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: genomic DNA (ix) FEATURE:
        (D) OTHER INFORMATION: N is inosine (xi) SEQUENCE DESCRIPTION: SEQ ID NO:11:

GTNAAYCCGA CWTTYGTNGT                                               20

(2) INFORMATION FOR SEQ ID NO:12:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: genomic DNA (ix) FEATURE:
        (D) OTHER INFORMATION: N is inosine (xi) SEQUENCE DESCRIPTION: SEQ ID NO:12:

GTNAAYCCGA CCTTYGTNGT                                               20

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Val Asn Pro Thr Phe Val Val
              5

(2) INFORMATION FOR SEQ ID NO:14:

(i) SEQUENCE CHARACTERISTICS:
        (A) LENGTH: 84 nucleic acids
        (B) TYPE: nucleotides

```
            (C) STRANDEDNESS: single
            (D) TOPOLOGY: linear (ii) MOLECULE TYPE: genomic DNA (xi) SEQUENCE DESCRIPTION: SEQ ID NO:14:

ATGAAGATGA AAAAGATAAC AAATTTGGTG TACATTTTGG TAGCCATTAC AACAAGTGTG      60

ATCTTTCAAT GGACTTGCAA TGCA                                            84

(2) INFORMATION FOR SEQ ID NO:15:

(i) SEQUENCE CHARACTERISTICS:
        (A) LENGTH: 946 nucleic acids
        (B) TYPE: nucleotides
        (C) STRANDEDNESS: single
        (D) TOPOLOGY: linear (ii) MOLECULE TYPE: genomic DNA (xi) SEQUENCE DESCRIPTION: SEQ ID NO:15:

GCAGACCTGA CTTTCACGGT GACTAAGAGT GGTACCAGCC AAAGCTACTC CACACTATTG      60

AATAGCTTTC GAGATAAAGT TAAAGATCCA AAACTAACAG GAACTTATGG ATTTCAAAAC     120

AATTTACCAG TTGTAGCTGC ACCCACAACA CCTGCTAAGT ATCTTTACAT TGATATTCAG     180

GCAGATAATG GAATAATCAC TGCTGCATTT GATAAAAACG ATCTCTATTA TATGGGTTAT     240

GCTCACACTG CAGATGGAGT CAAGAAGGTA CGTCTCTTCA AAGGCGCTCC AACTGACGTA     300

AAGTTGATTT TTCCCGATGT TACAAATAAA AACAATCGAT ATTATTCGAC CATTACTGGA     360

AACTATAATG ATCTTGGAGA TCGAGCCTCT GTAGGGTTGG GAGCTAAACC ACTTAATAAG     420

TTTATTAATG AAGAAATCTA TACAAAAAAG AAATTTGACA TTACAACAGA TAAAAAGCTA     480

GCGCTTATGG TCATCCAAAC TATTGCAGAA GCAGCGCGAT TTACATATAT TGAAGGTGAA     540

ATCGTGAGTA AATTCAGTGA TAATAGTGGA TTCAAATGTA ATGATAAAGC CAAGTCACTG     600

GAGAACAATT GGGAAAAAAC CAGTAAAACT GTCAAGAATT CTACTGGTCC TAGAATTGAT     660

TTGGAATTAA AAGATGAAAA TGGTAAAGTA GTCTGGAAAT GGTTACAAGT CGGAGAATTA     720

GTTGATGTCA TGGGGATTCT TAAATATCTT AAGTAGAATG GAAATGTCTT CATGTCATAT     780

AAGTATCTGT TTAGTAGCTG ATAATGAATA ATGAAAATGC AGCAATAAGC TAAGATATTA     840

CATATTGTTG TAAGTTCAAA GTTGTAACGA CTTTTGTTTT TTTAATACTT CTATCCCCTA     900

AAAAATATTT CACGTAAAAA AAAAAAAAAA AAAAAAAAA AAAAAA                    946

(2) INFORMATION FOR SEQ ID NO:16:

(i) SEQUENCE CHARACTERISTICS:
        (A) LENGTH: 1116 nucleic acids
        (B) TYPE: nucleotides
        (C) STRANDEDNESS: single
        (D) TOPOLOGY: linear (ii) MOLECULE TYPE: genomic DNA (xi) SEQUENCE DESCRIPTION: SEQ ID NO:16:

ATCCCATCAT TATATTTCCT CCATTGTTTT CTTATCCCAT CCTGTGAAAG CTTGAGCATT      60

ATATTGTTCA TCAACATGAA GATGAAAAAG ATAACAAATT TGGTGTACAT TTTGGTAGCC     120

ATTACAACAA GTGTGATCTT TCAATGGACT TGCAATGCAG TAAATCCAAC ATTCGTTGTG     180

ACAATGAGTG CTACCAATAA AAGCTACTCC ACTCTATTGA GTAGCTTTCG AGATGAAATT     240

CAAGATAAAA AATTAAAAGG AACTTATGGA TTTCAAAACG ATTTACCAGT TGTAGCTGCA     300

CCAACAAAAC CTGCTAAGTA TCTTTACATT GATATTCAGG CAGATAAGGG CATGATCACT     360
```

-continued

```
GCTGCGTTTA ATAAAAACGA TCTCTATTAT ATGGGTTATG CTCACACTGC TGATGGAGCC    420

AAGAAAGTAC GTCTCTTCAA AGGCGCTCCA ACTGACGTAA GGTTGATTTT TCCCGACGTT    480

ACAAATATAA ACAATCGATA TTATTCTACC ATTACTGGAA ACTATAATGA GCTTGGAGAT    540

CGAGCCTCTG TAGGGTTGGG AGCTAAACCA CTTAATAAGT TTATTAATGA AGAAATCTAT    600

ACAAAAAAGA AATTTGACAT ACAAACAGAT CAAAAGCTAG CGCTTATGGT CATCCAAACT    660

ATTGCAGAAG CAGCGCGATT TAAATATATT GAGGGTGAAA TCGTGGCTAA ATTTAGTGAT    720

AATAGTGGAT TCAAAGCTAA TCCTAAAGCC AAATCACTGG AGAACAATTG GGATAAAACC    780

AGTGAGACTG TCAAGGCATC TACTGGTCCT AGAATTGATT TGGAATTAAC ATATGGAAAT    840

GGTAATGTAG TATGGAAATG GTTTCAAGTC GGAGAATTAG TTGATGTCAT GGGGATTCTT    900

AAATATCTTA AGTAGAATGG AAATGTCTTC ATGTCATATA AGTATCTGTT TAGTAGCTGA    960

TAATGAATAA TGAAAATGCA ACAATAAGCT AAGATATTAC TTAGGGTTGT AATTTCAAAG   1020

TTGTAACGAC TTTTGTATGT TTAATACTTC TATCCCCTAA AAAATATTGC ACGTTTCCAA   1080

AAAAAAAAAA AAAAAAAAAA AAAAAAAAAA AAAAAA                            1116
```

Prestle, J. et al., Nucleic Acids Res., 1992, 20:3179–3182.
Lorenzetti et al., 1996, U.S. Pat. No. 5,529,932.
Legname et al., 1996, U.S. Pat. No. 5,501,970.

What is claimed is:

1. An isolated DNA sequence encoding antiviral protein amarandin 1 of *Amaranthus viridis* having the sequence of SEQ ID NO. 15.

2. An isolated DNA sequence encoding antiviral protein amarandin 2 of *Amaranthus viridis* having the sequence of SEQ ID NO. 16.

3. The isolated cDNA sequence according to claim 1, wherein said cDNA sequence comprises at least one restriction site for each of the enzymes:

KLESIN1-AflI, AluI, AseI, Asp718I, AsuI, BanI, BsmAI, BstXI, CfoI, ClaI, DdeI, DpnI, EarI, EcoRI, Fnu4HI, HinP1I, HinfI, HphI, KpnI, Ksp632I, MaeI, MaeII, MfeI, MseI, NlaIII, NlaIV, PleI, RsaI, Sau3AI, SstIII, TaqI, TspEI.

4. The isolated DNA sequence encoding antiviral protein amarandin 1 of *Amaranthus viridis* according to claim 1, wherein the nucleotides encoding the signal sequence are directly linked to the 5' end of the nucleotides that encode antiviral protein amarandin 1, and the nucleotides encoding the signal sequence have the following sequence:

ATGAAGATGA AAAAGATAAC AAATTTGGTG TACATTTTGG TAGCCATTAC AACAAGTGTG ATCTTTCAAT GGACTTGCAA TGCA (SEQ ID NO:14).

5. The isolated DNA sequence encoding antiviral protein amarandin 1 according to claim 1, wherein said DNA is a cDNA which encodes the following N-terminal amino acid sequence,

[1]Ala-Asp-Leu-Thr-Phe-Thr-Val-Thr-Lys-Asp-Gly[11]- (amarandin 1) (SEQ ID NO:1).

6. A hybrid vector comprising the DNA sequence according to claim 1, wherein said vector is capable of being transferred to and replicating in a host.

7. An expression vector comprising the DNA sequence according to claim 1 wherein said vector is plasmid pRSET obtainable from the *E. coli* strain KCTC0344BP.

8. A transformed bacterial host comprising the vector as claimed in claim 7.

9. The isolated DNA sequence according to claim 2, wherein said DNA sequence comprises at least one restriction site for each of the following AflI, AluI, AseI, AsuI, BclI, BsmAI, BstXI, CfoI, ClaI, DdeI, DpnI, DraI, EarI, Fnu4HI, HinP1I, HinfI, HphI, Ksp632I, MaeI, MaeII, MfeI, MseI, NlaIII, NlaIV, RsaI, Sau3AI, SstIII, TaqI and TspEI.

10. The isolated DNA sequence according to claim 2, wherein the nucleotides encoding the signal sequence are directly linked to the 5' end of the nucleotide that encode antiviral protein amarandin 2, and the nucleotides encoding the signal sequence have the following sequence:

ATGAAGATGA AAAAGATAAC AAATTTGGTG TACATTTTGG TAGCCATTAC AACAAGTGTG ATCTTTCAAT GGACTTGCAA TGCA (SEQ ID NO:14).

11. The isolated DNA sequence according to claim 2, wherein said DNA is a cDNA which encodes the following N-terminal amino acid sequence:

[1]Val-Asn-Pro-Thr-Phe-Val-Val-Thr-Met-Ser[10]- (amarandin 2) (SEQ ID NO:2).

12. A hybrid vector comprising the DNA according to claim 2, wherein said vector is capable of being transferred to and replicating in a host.

13. An expression vector comprising the DNA sequence according to claim 2, wherein said vector is plasmid pRSET obtainable from the *E. coli* strain KCTC0345BP.

14. A transformed bacterial host comprising the vector according to claim 12.

* * * * *